United States Patent [19]

Shimodaira et al.

[11] Patent Number: 4,782,890

[45] Date of Patent: Nov. 8, 1988

[54] HEAT PIPE

[75] Inventors: Saburo Shimodaira, Izumi; Isamu Uchida, Sakai; Minoru Hasegawa, Sakai; Koichiro Fukui, Sakai; Yuichi Furukawa, Sakai; Kazunari Noguchi, Sendai, all of Japan

[73] Assignee: Showa Aluminum Corporation, Osaka, Japan

[21] Appl. No.: 39,856

[22] Filed: Apr. 20, 1987

[30] Foreign Application Priority Data

Apr. 23, 1986 [JP] Japan ............................. 61-95391
Jul. 28, 1986 [JP] Japan ............................. 61-115589[U]
Jul. 28, 1986 [JP] Japan ............................. 61-115590[U]
Jul. 28, 1986 [JP] Japan ............................. 61-11591[U]
Jul. 28, 1986 [JP] Japan ............................. 61-115592[U]

[51] Int. Cl.$^4$ ............................................. F28D 15/02
[52] U.S. Cl. ................................. 165/104.27; 165/917
[58] Field of Search ................ 165/104.27, 134.1, 917

[56] References Cited

U.S. PATENT DOCUMENTS 4,455,998  6/1984  Kroontje et al. ................. 165/96
4,586,561  5/1986  Franco et al. .................. 165/104.27

FOREIGN PATENT DOCUMENTS 151884   11/1981  Japan ........................ 165/104.27
8102467  12/1982  Netherlands ................. 165/104.27
517774    6/1976  U.S.S.R. ..................... 165/104.27

Primary Examiner—Albert W. Davis, Jr.
Attorney, Agent, or Firm—Armstrong, Nikaido, Marmelstein & Kubovcik

[57] ABSTRACT

A heat pipe comprising a container having water enclosed therein as a working fluid and made of a material reactive with water to evolve hydrogen gas. The heat pipe is characterized in that the container has placed therein a solid oxidizing agent for oxidizing the hydrogen gas to water. The hydrogen gas produced by the reaction of the working fluid, i.e. water, with the container is oxidized to water by the oxidizing agent without remaining in the form of a gas within the condensing portion of the pipe.

19 Claims, 4 Drawing Sheets

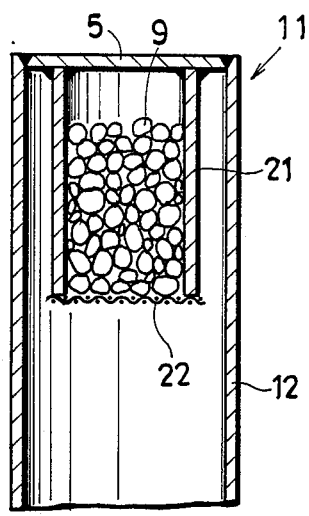
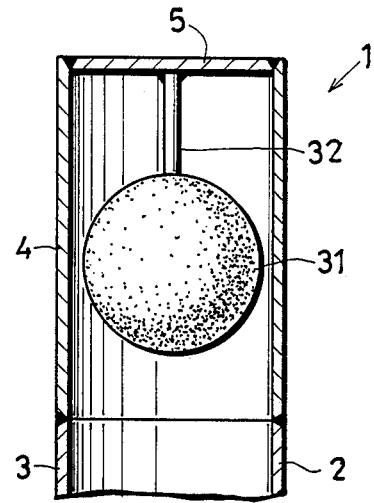
FIG.3  FIG.4
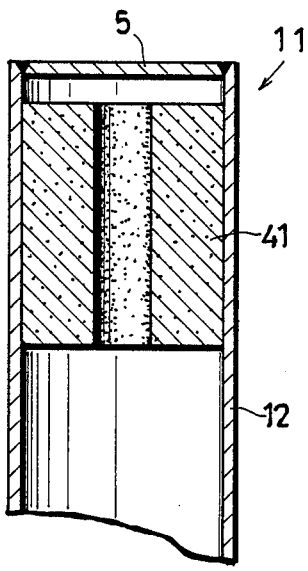
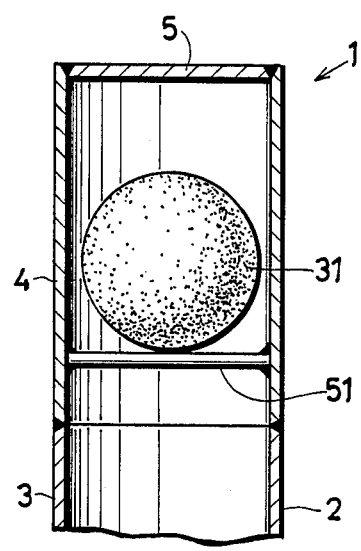
FIG.5  FIG.6 though the wall of the container in the form of atoms
HEAT PIPE

BACKGROUND OF THE INVENTION

The present invention relates to a heat pipe in the form of a container having water enclosed therein as a working fluid and made of iron, copper or the like which reacts with water to evolve hydrogen gas.

The term "iron" as used herein includes pure iron and also iron alloys such as stainless steel and carbon steel.

Heat pipes comprising an iron container having water enclosed therein as a working fluid are in wide use because of the high strength of the container and the high performance of water as the working fluid. However, such heat pipes have the problem that iron reacts with water to evolve hydrogen gas, impairing the performance of the heat pipe in a short period of time. More specifically, the evolved hydrogen gas diffuses through the wall of the container in the form of atoms and becomes partly released from the container at a constant rate, but a major portion of the hydrogen gas remains in and occupies the condensing portion within the container to impede condensation of vapor and lower the performance of the heat pipe. Such impairment becomes pronounced with time, rapidly shortening the life of the heat pipe. While the iron container is sometimes aluminized over the outer surface to provide protection against corrosion and also to attach thereto aluminum fins having a brazing layer formed by vacuum brazing, the hydrogen gas diffusing through the container wall is then prevented from escaping from the container by the aluminized coating.

Accordingly, the following means have heretofore been employed to prevent the evolution of hydrogen gas and to preclude deterioration of the heat pipe due to the evolution of hydrogen gas.

(1) Addition of an inhibitor to the working fluid, i.e. water, to inhibit the reaction between water and iron.

(2) Plating of the inner surface of the iron container with copper or like metal.

(3) Provison of a hydrogen occluding material within the container.

(4) Provision of a linear hydrogen passing member of Pd, or use of hydrogen-permeable Pd for forming the condensing portion to hold the interior of the container in communication with the outside.

However, the means (1) and (2), if used, are unable to inhibit the evolution of hydrogen gas, while the means (3) and (4) fail to fully occlude or release hydrogen gas when the heat pipe is used as high temperatures which result in evolution of an increased amount of hydrogen gas. Accordingly, it has been impossible to prevent the heat pipe from deterioration even with the use of means (1) to (4).

SUMMARY OF THE INVENTION

The main object of the present invention is to provide a heat pipe which is free of the foregoing problems and which retains the desired performance without deterioration over a prolonged period of time.

The present invention provides a heat pipe comprising a container having water enclosed therein as a working fluid and made of a material reactive with water to evolve hydrogen gas, the heat pipe being characterized in that the container has placed therein a solid oxidizing agent for oxidizing hydrogen gas to water.

According to the present invention, even when the working fluid, i.e. water, reacts with the container to produce hydrogen gas, the hydrogen gas is oxidized to water by the oxidizing agent, with the result that the heat pipe can be prevented from deterioration due to the evolved hydrogen gas. Further when the heat pipe has placed therein the oxidizing agent in such an amount as to oxidize the predicted total amount of hydrogen gas to be evolved, the heat pipe is operable reliably with the desired performance without impairment, over a long period of time. An increased quantity of hydrogen gas will be produced when the heat pipe is used at a high temperature, but the gas can be returned to water rapidly to inhibit the deterioration of the heat pipe.

The present invention will be described in greater detail with reference to the accompanying drawings.

BRIEF DESCRIPTION OF THE DRAWINGS

FIG. 3 is a view in vertical section showing the condensing portion of a third embodiment of the invention;

FIG. 4 is a view similar to FIG. 3 and showing a fourth embodiment of the invention;

FIG. 5 is a view similar to FIG. 3 and showing a fifth embodiment of the invention;

FIG. 6 is a view similar to FIG. 3 and showing a sixth embodiment of the invention;

DESCRIPTION OF THE PREFERRED EMBODIMENTS

Figures 1, 2:
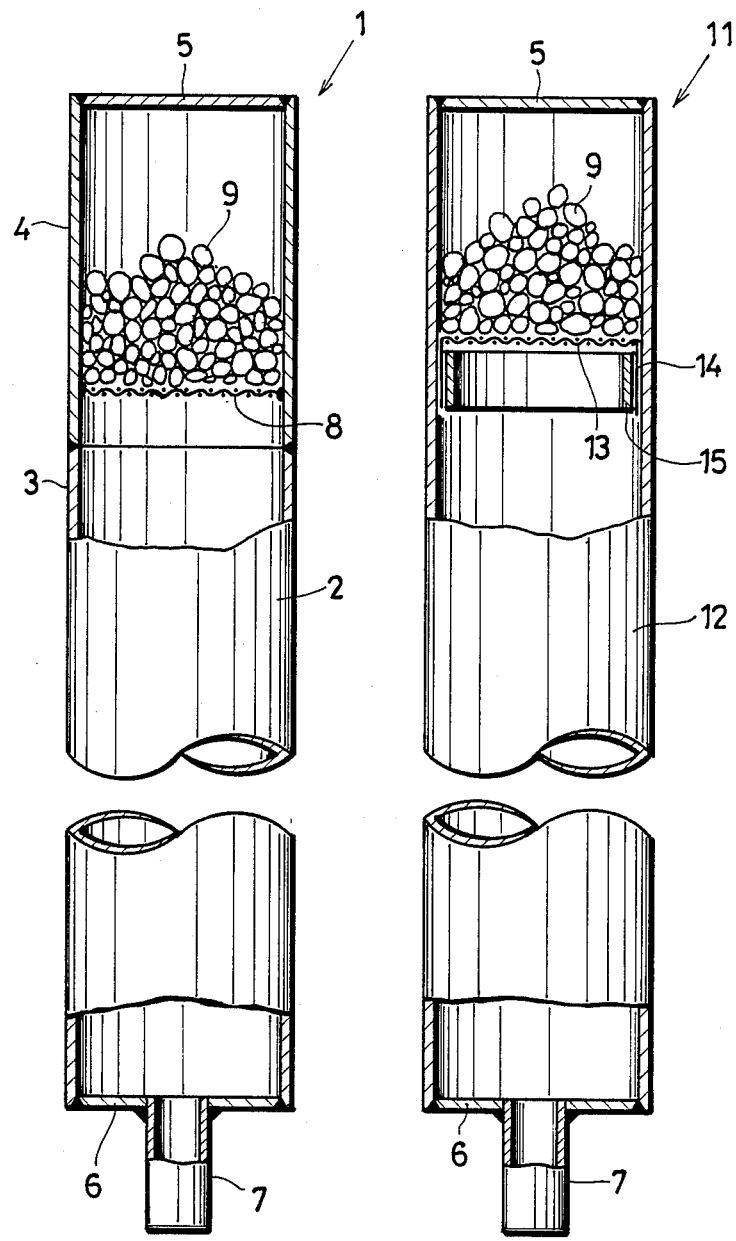
FIG. 1 is a front view partly broken away and showing a first embodiment of heat pipe of the invention.
FIG. 2 is a view similar to FIG. 1 and showing a second embodiment of the invention.

Throughout the drawings, like parts are designated by like reference numerals.

FIG. 1 shows a first embodiment of the invention, i.e. a heat pipe, which comprises an iron container 1 having enclosed therein pure water (not shown) as a working fluid. The container 1 comprises a container main body 2 including a long pipe 3 made, for example, of iron STB35 prescribed in JIS (Japanese Industrial Standards) G3461 and a short pipe 4 welded to one end of the long pipe 3 and made, for example, of iron STB35. The container 1 further comprises an end cap 5 welded to one end of the container main body 2 and made, for example, of iron SS41 prescribed in JIS G3101, and another end cap 6 welded to the other end of the main body 2, having a nozzle 7 and made, for example, of iron SS41. The material for forming the container 1 is not limited to iron but may be some other material, such as copper or copper alloy, which evolves hydrogen on reacting with water. The amount of pure water serving as the working fluid is preferably about 20% of the total interior volume of the container 1.

A net 8 of a metal such as copper is provided within the short pipe 4 of the container 1 at a portion thereof toward the long pipe 3 to partition the interior of the short pipe 4 across the axis of the pipe. The peripheral edge of the net 8 is joined to the inner surface of the short pipe 4 by brazing with silver or the like.

A granular oxidizing agent 9 for oxidizing hydrogen to water is placed in the space between the net 8 and the end cap 5. The size of the granules of the oxidizing agent 9 is larger than the mesh size of the net 8 so that the agent 9 will not pas through the meshes. Thus, the net 8 restrains the oxidizing agent 9 from moving toward the long pipe 3. The oxidizing agent to be used is one which causes the reaction of: $H_2+MO \rightarrow H_2O+M$ wherein M is a metal element. Examples of preferred oxidizing agents are copper oxides, such as $Cu_2O$ and $CuO$, which exert no adverse effect on the performance of the heat pipe when placed therein, are inexpensive and effectively oxidize hydrogen gas. The oxidizing agent 9 should be present in an amount sufficient to oxidize the hydrogen to be evolved within the heat pipe. For example, in a three-meter-long heat pipe in the form of an iron container having water enclosed therein, up to 2 c.c./day of hydrogen gas is evolved even if the inner surface of the container is coated with a protective film. Accordingly, if this heat pipe is to be used for 10 years, 30 g of CuO (at least 0.32 mol) should be placed into the container.

The heat pipe 1 is used with the short pipe side serving as a condensing portion and the opposite side as an evaporating portion. The hydrogen gas produced by the reaction of the working fluid, i.e. water, and the container 2 is oxidized to water by the oxidizing agent 9.

FIG. 2 shows a second embodiment of the invention, i.e., a heat pipe comprising a container 11 The container 11 comprises a container main body 12 in the form of a pipe made, for example, of iron STB35 of JIS. A net 13 of a metal such as copper is provided within the container 11 at a portion thereof close to an end cap 5 to partition the interior of the main body 12. The peripheral portion of the net 13 is bent toward the other end of the main body 12 so as to extend along the inner surface of the main body 12. The bent edge portion 14 of the net is held between the container main body 12 and a ring 15 fixedly bearing against the inner surface of the main body 12, whereby the net 13 is secured to the container main body 12.

Provided in the container 11 between the net 13 and the end cap 5 is an oxidizing agent 9 in the form of granules larger than the meshes of the net 13. The net 13 prevents the oxidizing agent 9 from moving toward the other end of the container 11.

With reference to FIG. 3 showing a third embodiment of the invention, a tube 21 for accommodating an oxidizing agent is provided within a container 11 at a position close to an end cap 5. One end of the tube 21 is welded to the inner surface of the end cap 5. The opening of the tube 21 at this end is closed with the cap 5. The other open end of the tube 21 is covered with a net 22 of a metal such as copper. The net is joined to the other end by brazing. The oxidizing agent 9 placed in the tube 21 is in the form of granules larger than the meshes of the net 22, which therefore, prevents the agent 9 from moving toward the other end of the container 11.

The oxidizing agent used in the first to third embodiments and in the form of granules may alternatively be a powder which is larger in particle size than the mesh size of the net.

With reference to FIG. 4 showing a fourth embodiment of the invention, the container main body 2 shown comprises long and short two pipes 3 and 4 as in the first embodiment. Disposed within the short pipe 4 is a substantially spherical porous block 31 which is prepared by sintering a powdery oxidizing agent. A bar 32 parallel with the axis of the container main body 2 has one end secured to the inner surface of an end cap 5 and the other end fixedly provided with the porous body 31.

With reference to FIG. 5 showing a fifth embodiment of the invention, the container main body 12 shown comprises a single pipe as is the case with the second embodiment. A tubular porous block 41 prepared by sintering a powdery oxidizing agent is provided within the container main body 12 at one end thereof close to an end cap 5 and is fixed to the main body 12. The block 41 is disposed concentrically with the container main body 12. The porous block 41 has an outside diameter slightly larger than the inside diameter of the main body 12 and is forcibly fitted into the main body 12, whereby the block 41 is secured to the main body. Alternatively, the porous block 41 is fixed in position by making the outside diameter of the block 41 slightly smaller than the inside diameter of the main body 12, placing the block into the main body 41 and thereafter enlarging the porous block 41 radially outward into pressing contact with the inner surface of the main body 12.

With reference to FIG. 6 showing a sixth embodiment of the invention, the container 1 shown is similar to that of the first embodiment and has, within a short pipe 4 at a position close to a long pipe 3, a restraining bar 51 intersecting the axis of the pipe 4 at right angles therewith. The spaces between the bar 51 and the inner peripheral surface of the short pipe 4 are smaller than a porous block 31 of oxidizing agent which is the same as the block 31 of the fourth embodiment. The porous block 31 is disposed between an end cap 5 and the restraining bar 51.

Figure 7:
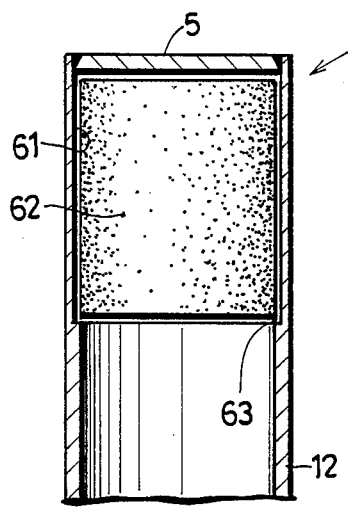
FIG. 7 is a view similar to FIG. 3 and showing a seventh embodiment of the invention.

With reference to FIG. 7 showing a seventh embodiment of the invention, the container main body 12 shown is similar to that of the second embodiment. The main body 12 has an enlarged portion 61 having a larger inside diameter, positioned close to an end cap 5 and formed by cutting the inner peripheral surface of the main body 12 over a specified length. A porous block 62 in the form of a solid cylinder and prepared by sintering a powdery oxidizing agent is accommodated in the enlarged portion 61. The porous block 61 has an outside diameter smaller than the inside diameter of the enlarged portion 61 but larger than the inside diameter of the other portion of the main body 12. A stepped portion 63 projecting inward from the inner peripheral surface of the enlarged portion 61 is formed on the inner surface of the main body 12 at the boundary between the enlarged portion 61 and the other portion. The stepped portion 63 prevents the porous block 62 from moving toward the other end of the main body 12.

Figure 8:
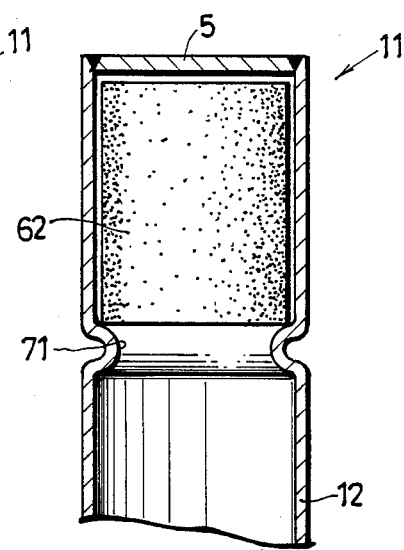
FIG. 8 is a view similar to FIG. 3 and showing an eighth embodiment of the invention.

With reference to FIG. 8 showing an eighth embodiment of the invention, the container main body 12 shown is beaded a the portion thereof at a specified distance from an end cap 5, whereby an annular inwardly projecting ridge 71 is formed over the entire inner peripheral surface of the main body 12. A solid cylindrical porous block 62 similar to the one included in the seventh embodiment and prepared by sintering a powdery oxidizing agent is disposed within the main body 12 between the ridge 71 and the end cap 5. The outside diameter of the porous body 62 is smaller than the inside diameter of the container main body 12 and larger than the inside diameter of the ridge 71. The ridge 71 on the inner surface of the container main body 12 prevents the porous block 62 from moving toward the other end of the main body 12. Thus, the ridge 71 serves as a step for restraining the porous block 62.

Figure 9:
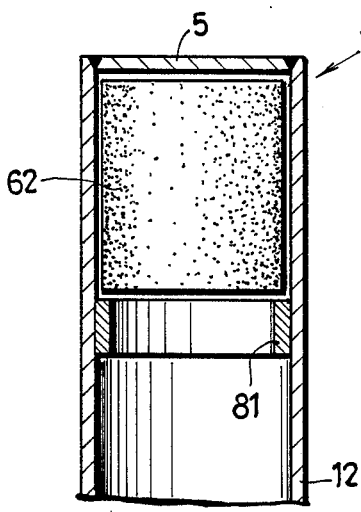
FIG. 9 is a view similar to FIG. 3 and showing a ninth embodiment of the invention.

With reference to FIG. 9 showing a ninth embodiment of the invention, the container main body 12 shown has placed therein a metal ring 81 at a specified distance from an end cap 5. The ring 81 is radially outwardly enlarged and is thereby secured to the main body 12. A solid cylindrical porous body 62 similar to that of the seventh embodiment and prepared by sintering a powdery oxidizing agent is disposed within the main body 12 between the ring 81 and the end cap 5. The porous block 62 has an outside diameter smaller than the inside diameter of the container main body 12 but larger than the inside diameter of the ring 81. The ring 81 on the inner surface of the main body 12 prevents the porous block 62 from moving toward the other end of the main body 12. Thus, the ring 81 serves as a stepped portion for preventing the movement of the porous block 62.

Figure 10:
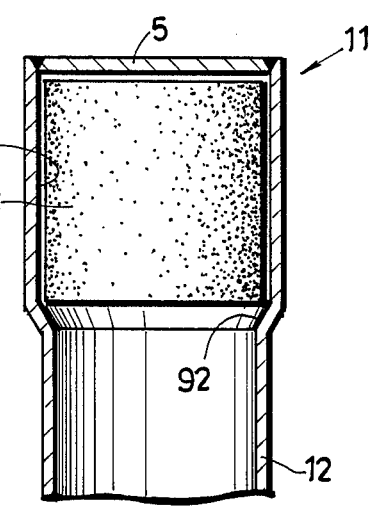
FIG. 10 is a view similar to FIG. 3 and showing a tenth embodiment of the invention.

With reference to FIG. 10 showing a tenth embodiment of the invention, the container main body 12 shown is radially enlarged over an end portion of specified length close to an end cap 5 to provide an enlarged portion 91. A solid cylindrical porous body 62 similar to that of the seventh embodiment and prepared by sintering a powdery oxidizing agent is accommodated in the enlarged portion 91. The porous block 62 has an outside diameter smaller than the inside diameter of the enlarged portion 91 but larger than the inside diameter of the other portion of the main body 12. An inclined stepped portion 92 inwardly projecting from the inner peripheral surface of the enlarged portion 91 and formed on the inner peripheral surface of the main body at the boundary between the portion 91 and the other portion prevents the porous block 62 from moving toward the other end of the container main body 12.

Figures 11, 12:
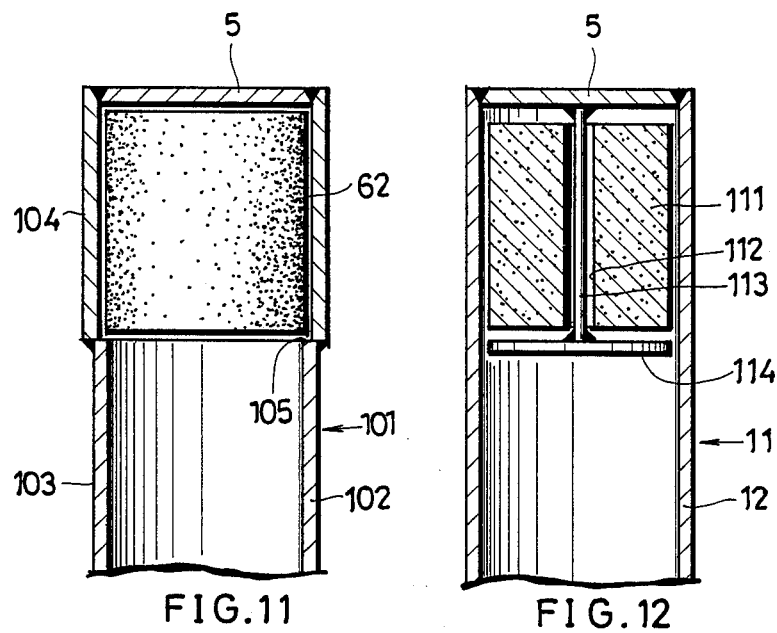
FIG. 11 is a view similar to FIG. 3 and showing an eleventh embodiment of the invention.
FIG. 12 is a view similar to FIG. 3 and showing a twelfth embodiment of the invention.

With reference to FIG. 11 showing an eleventh embodiment of the invention, the main body 102 of the container shown and indicated at 101 comprises long and short two pipes 103, 104 made, for example, of iron STB35 of JIS. The short pipe 104 has an inside diameter larger than the inside diameter of the long pipe 103 but smaller than the outside diameter of the pipe 103. The portion of the end face of the long pipe 103 including the inner peripheral edge thereof is exposed to the interior of the short pipe 104. The exposed portion is indicated at 105. A solid cylindrical porous block 62 similar to that of the seventh embodiment and prepared by sintering a powdery oxidizing agent is accommodated in the short pipe 104. The porous block 62 has an outside diameter smaller than the inside diameter of the short pipe 104 but larger than the inside diameter of the long pipe 103. The exposed end-face portion 105 of the long pipe 103 serves as a stepped portion for restraining the porous block 62 from moving toward the other end of the container main body 102.

With reference to FIG. 12 showing a twelfth embodiment of the invention, the container main body 12 shown and similar to that of the fifth embodiment has accommodated in one end portion thereof close to an end cap 5 a hollow cylindrical porous block 111 prepared by sintering a powdery oxidizing agent. The porous block 11 has a bore 112 extending therethrough in parallel with the axis of the main body 12. A bar 113 extending through the bore 112 has one end welded to the end cap 5 and the other end projecting out from the bore 112. A disklike stopper 114 is welded to the projecting end for restraining the porous block 111 from moving toward the other end of the main body 12.

With this embodiment, the disklike stopper 114 may be replaced by at least one rodlike stopper attached to the end of the bar 113.

The second to twelfth embodiments are used with the oxidizing agent accommodating side serving as a condensing portion and the other side as an evaporating portion. The hydrogen gas resulting from the reaction of the working fluid, i.e. water, with the container is oxidized to water.

Although the embodiments described above are all of the wickless type, the present invention can be embodied as heat pipes having a wick.

Further according to the foregoing embodiments, the oxidizing agent is disposed in the condensing portion, but the agent need not always be positioned in this portion.

EXAMPLE 1

A heat pipe having the construction of the first embodiment was used.

Prepared for the fabrication of the heat pipe were a long pipe 3 measuring 31.8 mm in length, 4.5 mm in wall thickness and 2900 mm in length and made of iron STB35 prescribed in JIS G3461, and a short pipe 4 measuring 31.8 mm in diameter, 4.5 mm in wall thickness and 100 mm in length and made of iron STB35. The inner surfaces of these pipes were brushed with a wire brush and thereafter degreased with acetone. A 80-mesh copper net 8 prescribed in JIS H6102 was blazed, to the inner side of the short pipe 4. An oxidizing agent 9 comprising $CuO$ and in the form of granules larger than the meshes of the net 8 was placed into the short pipe 4. An end cap 5 was then welded to one end of the short pipe 4, and the other end of the short pipe 4 was welded to one end of the long pipe 3. An end cap 6 provided with a nozzle 7 was then welded to the other end of the long pipe 3 to obtain a container 1. Pure water serving as a working fluid was enclosed in the container 1 via the nozzle 7. Thus, the heat pipe was fabricated.

Figure 13:
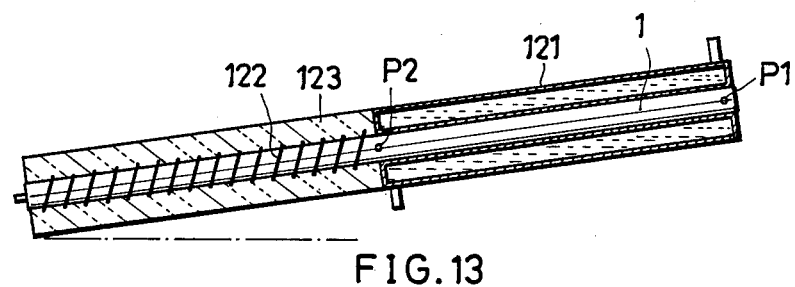
FIG. 13 is a front view partly broken away and showing a method of testing the heat pipe of FIG. 1 for the evaluation of its performance.
Figure 14:
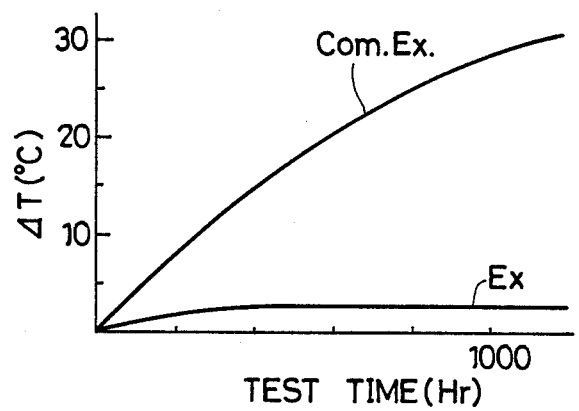
FIG. 14 is a graph showing the test result achieved by the heat pipe of FIG. 1 and the result attained by a comparative example.

To check the heat pipe for performance, a water-cooling jacket 121 was provided around one-half portion of the heat pipe toward its condensing side, and an electric heater wire 122 was wound around the other half-portion of the pipe toward its evaporating side. The heater wire 122 was then covered with a heat insulating material 123. The heat pipe was then installed as inclined by 6 degrees from a horizontal plane, with the end of the pipe at the condensing side positioned at a higher level (see FIG. 13). Cooling water was then passed through the jacket 121 to cool one half of the heat pipe, while heating the other half to 240° C. with the heater wire 122. The temperature of the condensing portion at a point P1 20 mm away from its outer end and the temperature of the pipe at the lengthwise midportion thereof outside the jacket 121, i.e. at a point P2 as shown in FIG. 13, were measured at a given time interval to determine the temperature difference ΔT between the two points P1 and P2. At this time, the amount of heat transfer from the evaporating portion to the condensing portion was adjusted to 4000 W at all times. FIG. 14 shows the result.

COMPARATIVE EXAMPLE

A heat pipe having substantially the same construction as the pipe used in the above example was used except that no oxidizing agent was placed in the condensing portion. The pipe was checked for performance under the same conditions as above, with the result shown in FIG. 14.

The graph of FIG. 14 reveals that the product of the invention having the oxidizing agent 9 placed in the condensing portion exhibits a temperature difference ΔT of about 3° C. even after the lapse of 1000 hours and therefore remains satisfactory in heat transfer efficiency, whereas in the case of the comparative example, the temperature difference ΔT increases considerably, indicating that the heat transfer performance becomes impaired in a short period of time.

What is claimed is:

1. A heat pipe comprising a container having water enclosed therein as a working fluid and made of a material reactive with water to evolve hydrogen gas, the heat pipe being characterized in that the container has placed therein a solid oxidizing agent for oxidizing the hydrogen gas to water.

2. A heat pipe as defined in claim 1 wherein the oxidizing agent is disposed within the container at the portion thereof serving as its condensing portion.

3. A heat pipe as defined in claim 1 wherein the oxidizing agent is a copper oxide.

4. A heat pipe as defined in claim 1 wherein the oxidizing agent is granular.

5. A heat pipe as defined in claim 1 wherein the oxidizing agent is powdery.

6. A heat pipe as defined in claim 1 wherein the oxidizing agent is a granular copper oxide.

7. A heat pipe as defined in claim 1 wherein the oxidizing agent is a powdery copper oxide.

8. A heat pipe as defined in claim 1 wherein a net is provided within the container and positioned at a specified distance from one end thereof for partitioning the interior of the container, and the oxidizing agent is provided between the net and said one end of the container and is in the form of granules larger than the meshes of the net.

9. A heat pipe as defined in claim 1 wherein a net is disposed within the container and positioned at a specified distance from one end thereof for partitioning the interior of the container, and the oxidizing agent is provided between the net and said one end of the container and is in the form of particles larger than the meshes of the net.

10. A heat pipe as defined in claim 1 wherein the container comprises a container main body in the form of a pipe and an end cap closing each of opposite open ends of the main body, and a tube for accommodating the oxidizing agent has one open end secured to and closed by the inner surface of the end cap at one end, the other open end of the accommodating tube being closed with a net, the oxidizing agent being accommodated in the tube and being in the form of granules larger than the meshes of the net.

11. A heat pipe as defined in claim 1 wherein the container comprises a container main body in the form of a pipe and an end cap closing each of opposite open ends of the main body, and a tube for accommodating the oxidizing agent has one open end secured to and closed by the inner surface of the end cap at one end, the other open end of the accommodating tube being closed with a net, the oxidizing agent being accommodated in the tube and being in the form of particles larger than the meshes of the net.

12. A heat pipe as defined in claim 1 wherein the oxidizing agent is powdery and sintered into a porous block, and the porous block is placed in the container.

13. A heat pipe as defined in claim 12 wherein the oxidizing agent is a copper oxide.

14. A heat pipe as defined in claim 12 wherein the container comprises a container main body in the form of a pipe and an end cap closing each of opposite open ends of the main body, and a bar has one end secured to the inner surface of the end cap at one end of the main body, the porous block being fixed to the other end of the bar.

15. A heat pipe as defined in claim 12 wherein the porous block is in the form of a hollow cylinder and is secured to the peripheral wall of the container.

16. A heat pipe as defined in claim 12 wherein the porous block of oxidizing agent is disposed in an interior portion of the container close to its one end, and restraining means is provided within the container at a specified distance from said one end thereof for restraining the porous block from moving toward the other end of the container.

17. A heat pipe as defined in claim 16 wherein the restraining means is at least one bar secured to the peripheral wall of the container.

18. A heat pipe as defined in claim 16 wherein the restraining means is a stepped portion formed on the peripheral wall of the container and projecting inward from the inner peripheral surface of the container portion having the porous block accommodated therein.

19. A heat pipe as defined in claim 16 wherein the container comprises a container main body in the form of a pipe and an end cap closing each of opposite open ends of the main body, and the restraining means is a stopper attached to one end of a bar, the bar extending through the porous block and secured at the other end thereof to the end cap at one end of the main body, the porous body being engageable with the stopper.

* * * * *